US010457320B2

(12) United States Patent
Shiino

(10) Patent No.: US 10,457,320 B2
(45) Date of Patent: Oct. 29, 2019

(54) WATER DETECTION SYSTEM AND ELECTRIC POWER STEERING APPARATUS

(71) Applicant: HITACHI AUTOMOTIVE SYSTEMS, LTD., Hitachinaka-shi, Ibaraki (JP)

(72) Inventor: Kohtaro Shiino, Isehara (JP)

(73) Assignee: HITACHI AUTOMOTIVE SYSTEMS, LTD., Hitachinaka-Shi (JP)

( * ) Notice: Subject to any disclaimer, the term of this patent is extended or adjusted under 35 U.S.C. 154(b) by 238 days.

(21) Appl. No.: 15/533,427

(22) PCT Filed: Nov. 27, 2015

(86) PCT No.: PCT/JP2015/083317
§ 371 (c)(1),
(2) Date: Jun. 6, 2017

(87) PCT Pub. No.: WO2016/098557
PCT Pub. Date: Jun. 23, 2016

(65) Prior Publication Data
US 2017/0341681 A1    Nov. 30, 2017

(30) Foreign Application Priority Data

Dec. 16, 2014 (JP) ................................. 2014-254426

(51) Int. Cl.
*B62D 5/04* (2006.01)
*H02K 11/33* (2016.01)
(Continued)

(52) U.S. Cl.
CPC ........ *B62D 5/0481* (2013.01); *B60R 16/0232* (2013.01); *B62D 5/04* (2013.01);
(Continued)

(58) Field of Classification Search
CPC .... B62D 5/0481; B62D 5/0424; B62D 5/046; B62D 5/04; H02K 11/33; H02K 7/116;
(Continued)

(56) References Cited

U.S. PATENT DOCUMENTS

2009/0187314 A1* 7/2009 Kitamura ............ B60R 16/0231
701/45
2017/0050669 A1* 2/2017 Asakura ............... B62D 5/0481
(Continued)

FOREIGN PATENT DOCUMENTS

JP    H06-094799 A    4/1994
JP    2006-111032 A   4/2006
(Continued)

*Primary Examiner* — Jacob D Knutson
(74) *Attorney, Agent, or Firm* — Foley & Lardner LLP

(57) ABSTRACT

Provided is a water detection system and an electric power steering apparatus capable of preventing or reducing complication of an apparatus with respect to a water detection system including a water detection element and a determination circuit positioned separately from each other. The water detection system includes a transmission-side unit provided in an apparatus mounted on a vehicle of the electric power steering apparatus and including a water detection element, and a reception-side unit spaced apart from the transmission-side unit and including a determination circuit. The transmission-side unit wirelessly transmits an output signal of the water detection element, and the reception-side unit receives the output signal wirelessly transmitted from the transmission-side unit.

29 Claims, 9 Drawing Sheets

(51) Int. Cl.
  *B60R 16/023*   (2006.01)
  *F16H 25/24*    (2006.01)
  *G01N 29/02*    (2006.01)
  *H01R 13/03*    (2006.01)
  *H02K 7/116*    (2006.01)
  *B60R 16/033*   (2006.01)
  *B62D 1/16*     (2006.01)
  *B62D 3/12*     (2006.01)
  *F16H 25/22*    (2006.01)

(52) U.S. Cl.
  CPC ........... *B62D 5/046* (2013.01); *B62D 5/0424* (2013.01); *F16H 25/2418* (2013.01); *G01N 29/02* (2013.01); *H01R 13/03* (2013.01); *H02K 7/116* (2013.01); *H02K 11/33* (2016.01); *B60R 16/033* (2013.01); *B62D 1/16* (2013.01); *B62D 3/12* (2013.01); *F16H 25/2204* (2013.01)

(58) Field of Classification Search
  CPC . H01R 13/03; B60R 16/0232; F16H 25/2418; G01N 29/02
  USPC .......................................................... 180/446
  See application file for complete search history.

(56) References Cited

U.S. PATENT DOCUMENTS

2017/0250525 A1* 8/2017 Ricci ..................... H04W 4/90
2018/0319227 A1* 11/2018 Abdel-Baset ......... B60C 23/002

FOREIGN PATENT DOCUMENTS

| JP | 2006111032 A | * | 4/2006 |
| JP | 2006-327421 A | | 12/2006 |
| JP | 2010-132220 A | | 6/2010 |
| JP | 2011-088587 A | | 5/2011 |
| JP | 2011088587 A | * | 5/2011 |
| JP | 2012-224274 A | | 11/2012 |

* cited by examiner

WATER DETECTION SYSTEM AND ELECTRIC POWER STEERING APPARATUS

TECHNICAL FIELD

The present invention relates to a water detection system and an electric power steering apparatus.

BACKGROUND ART

Conventionally, there have been known electric power steering apparatuses including a water detection element provided in a gear housing to detect water leaked into the gear housing. An output signal of the water detection element is transmitted to a determination circuit provided outside the gear housing via wirings laid inside and outside the gear housing. The determination circuit determines whether there is the leak of the water into the gear housing based on the output signal of the water detection element. PTL 1 discusses one example regarding the above-described technique.

CITATION LIST

Patent Literature

PTL 1: Japanese Patent Application Public Disclosure No. 2012-224274

SUMMARY OF INVENTION

Technical Problem

There are needs desiring prevention or a reduction of complication of the apparatus with respect to the water detection system including the water detection element and the determination circuit positioned separately from each other.

An object of the present invention is to provide a water detection system and an electric power steering apparatus capable of preventing or reducing the complication of the apparatus.

Solution To Problem

One embodiment of the present invention includes a transmission-side unit provided in an apparatus mounted on a vehicle and including a water detection element, and a reception-side unit spaced apart from the transmission-side unit and including a determination circuit. The transmission-side unit wirelessly transmits an output signal of the water detection element, and the reception-side unit receives the output signal wirelessly transmitted from the transmission-side unit.

Therefore, the present invention can prevent or reduce the complication of the apparatus.

DESCRIPTION OF EMBODIMENTS

First Embodiment

[Electric Power Steering Apparatus]

Figure 1:
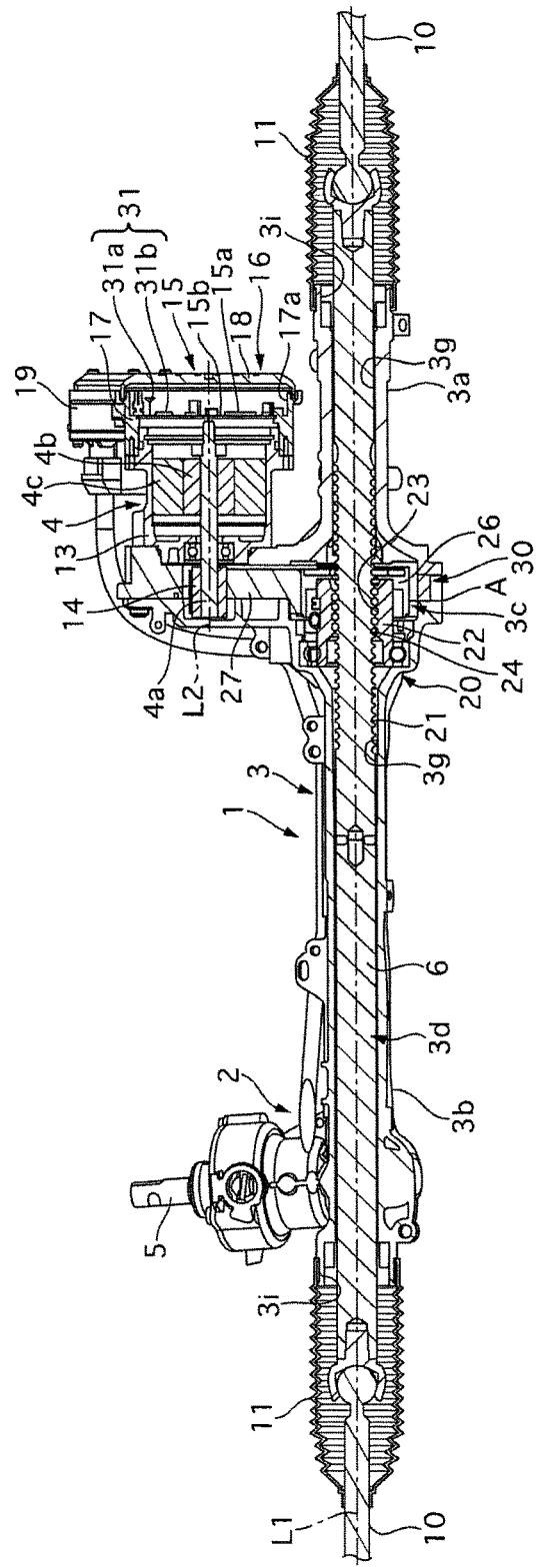
FIG. 1 is a front view partially including a cross-sectional view that illustrates an electric power steering apparatus 1 according to a first embodiment.
Figure 2:
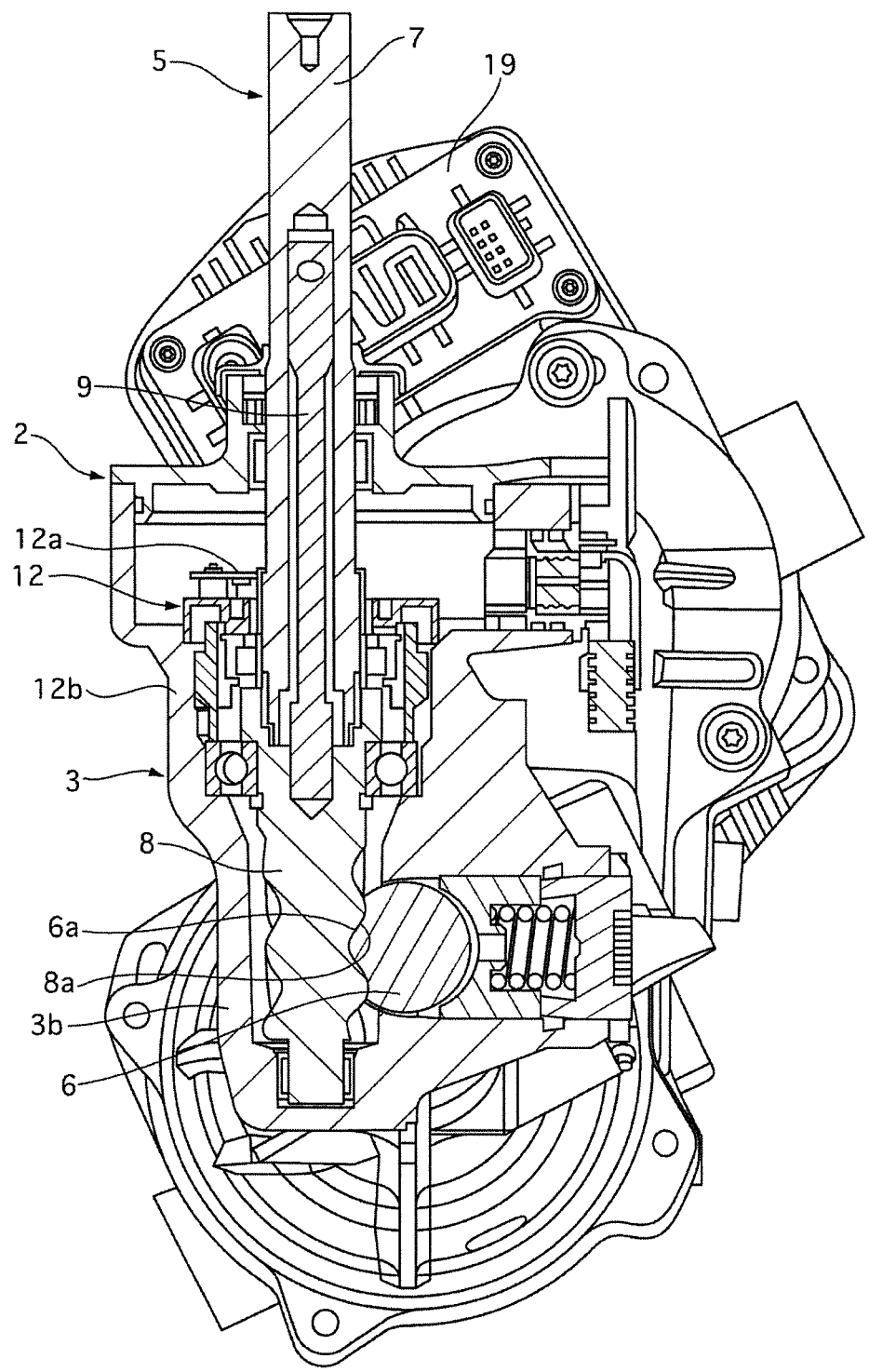
FIG. 2 is a cross-sectional view of a steering mechanism 2 of a gear housing 3 according to the first embodiment.
Figure 3:
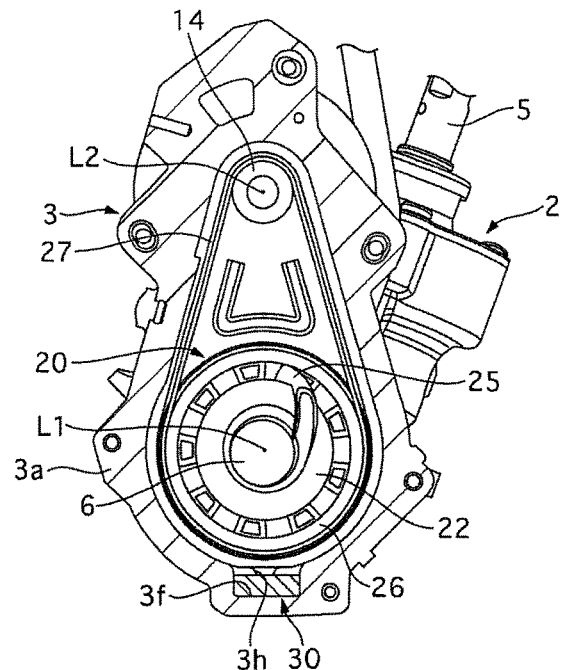
FIG. 3 is a cross-sectional view of a ball screw mechanism 20 of the gear housing 3 according to the first embodiment.
Figure 4:
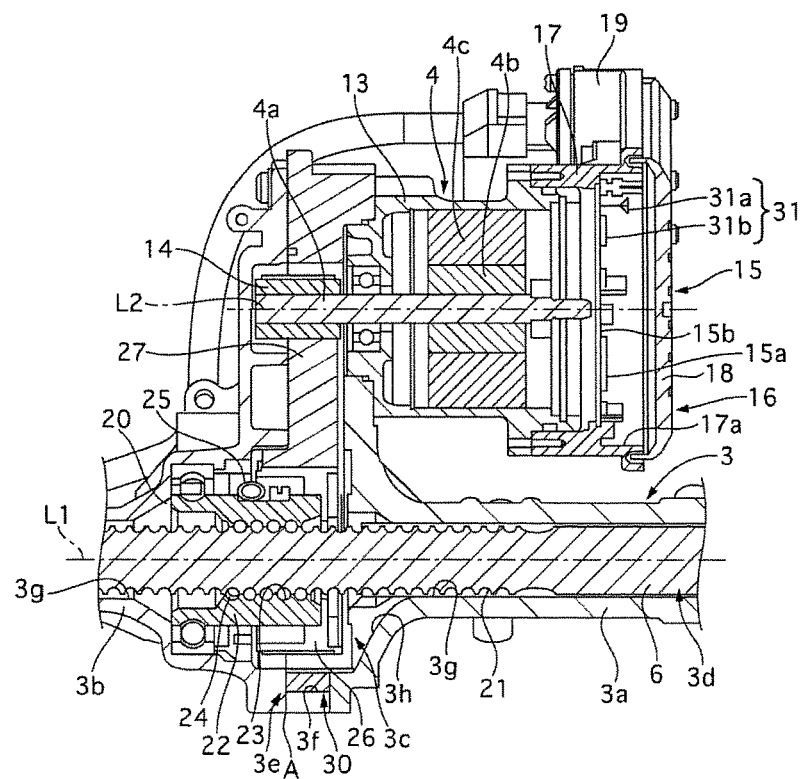
FIG. 4 is an enlarged view of main portions illustrated in FIG. 1.

FIG. 1 is a front view partially including a cross-sectional view that illustrates an electric power steering apparatus 1 according to a first embodiment. FIG. 2 is a cross-sectional view of a steering mechanism 2 of a gear housing 3 according to the first embodiment. FIG. 3 is a cross-sectional view of a ball screw mechanism 20 of the gear housing 3 according to the first embodiment. FIG. 4 is an enlarged view of main portions illustrated in FIG. 1. The electric power steering apparatus 1 according to the first embodiment is mounted on a vehicle that uses an engine as a driving source thereof. The electric power steering apparatus 1 includes the steering mechanism 2, the gear housing 3, and an electric motor 4. The steering mechanism 2 turns a turning target wheel according to a rotation of a steering wheel. The steering mechanism 2 is contained in the gear housing 3. The electric motor 4 provides a steering force to the steering mechanism 2.

The steering mechanism 2 includes a steering shaft 5 and a rack bar (a wheel turning shaft) 6. The steering shaft 5 includes a steering shaft bar 7 and a pinion shaft 8. The steering shaft bar 7 rotates integrally with the steering wheel. The pinion shaft 8 is connected to the steering shaft bar 7 via a torsion bar 9. A pinion gear 8a is formed around an outer periphery of the pinion shaft 8. The pinion gear 8a is meshed with a rack gear 6a formed over a predetermined range of an outer periphery of the rack bar 6. The rack bar 6 is axially displaced in a width direction of a vehicle body according to a rotation of the steering shaft 5. The rack bar 6 is formed with use of a ferrous metallic material, such as a steel material. Ends of a pair of tie rods 10 and 10 are connected to both ends of the rack bar 6, respectively.

A part of the steering shaft 5 and a part of the rack bar 6 are contained in the gear housing 3. The gear housing 3 has a structure divided into two portions, in which a first gear housing portion 3a and a second gear housing portion 3b are jointed in abutment with each other in an axial direction of the rack bar 6 (the vehicle width direction). The first gear housing portion 3a and the second gear housing portion 3b are formed with use of aluminum alloy by metal mold casting. Opening portions 3i and 3i are provided at a pair of ends of the gear housing 3. The rack bar 6 penetrates through the opening portions 3i and 3i. Inner ends of dust boots 11 in the vehicle width direction are fixed to the pair of ends of the gear housing 3, respectively. The dust boots 11 are provided to prevent or reduce a leak of water from outside into the gear housing 3. The dust boots 11 are each formed into a bellows-like annular shape with use of synthetic resin. Outer ends of the dust boots 11 in the vehicle width direction are fixed to inner ends of the tie rods 10 in the vehicle width direction, respectively. A torque sensor 12 is provided at the steering shaft 5. The torque sensor 12 detects a steering torque generated at the steering mechanism 2 (a torsion bar toque). The torque sensor 12 includes the torsion bar 9, a detection unit 12a, and a sensor housing 12b. The detection unit 12a detects a torsional amount of the torsion bar 9. The sensor housing 12b is provided on the vertically upper side of the second gear housing portion 3b with the power steering apparatus 1 mounted on the vehicle.

A three-phase brushless motor is used as the electric motor 4. The electric motor 4 is contained in a motor housing 13. The motor housing 13 is joined to the first gear housing portion 3a. The electric motor 4 includes a motor shaft 4a, a rotor 4b, and a stator 4c. The motor shaft 4a is provided integrally with the rotor 4b. An input pulley 14 is attached to the motor shaft 4a. The input pulley 14 is cylindrically formed. The rotor 4b is supported rotatably around an axial direction of the motor shaft 4a relative to the motor housing 13. The stator 4c is fixed to the motor housing 13. Driving of the electric motor 4 is controlled by a controller 15 including a microcomputer 15a mounted thereon.

The controller 15 includes an ECU housing 16. The ECU housing 16 includes an ECU housing main body portion 17, a cover member 18, and a connector portion 19. The ECU housing main body portion 17 is joined to the motor housing 13. An ECU housing main body opening portion 17a is provided on an opposite side of the ECU housing main body portion 17 from the electric motor 4. The ECU housing main body opening portion 17a is formed so as to expose the inside of the ECU housing main body portion 17. A circuit substrate 15b is contained inside the ECU housing main body portion 17. The microcomputer 15a including a CPU, a RAM, a ROM, and the like, and a not-illustrated power module are mounted on the circuit substrate 15. The ECU housing main body opening portion 17a is closed by the cover member 18. The ECU housing main body portion 17 and the cover member 18 are formed with use of aluminum alloy.

The connector portion 19 is provided so as to be exposed to outside the ECU housing main body portion 17. The connector portion 19 is formed with use of synthetic resin. A power system harness is connected to the connector portion 19. The power system harness is used to supply power from the vehicle side. Further, a signal system harness is connected to the connector portion 19. The signal system harness is used to input an output signal of the torque sensor 12 and a signal indicating information regarding a running state of the vehicle (a vehicle speed and the like). The power and the signals input to the connector portion 19 are input to the controller 15 via a not-illustrated bus bar. The controller 15 calculates, based on each of the input signals, a motor torque instruction for controlling the driving of the electric motor 4, and supplies power according to the motor torque instruction to the electric motor 4.

A ball screw mechanism 20 is provided between the electric motor 4 and the rack bar 6. The ball screw mechanism 20 is contained in a ball screw mechanism containing portion 3c of the gear housing 3. The ball screw mechanism containing portion 3c is provided vertically above a joint surface A where the first gear housing portion 3c and the second gear housing portion 3b are joined to each other, with the gear housing 3 mounted on the vehicle. The first gear housing portion 3a includes an opening portion 3e facing the joint surface A. A recessed portion 3f facing the opening portion 3e is provided at a vertically lower end of the first gear housing portion 3a. The recessed portion 3f is formed so as to be recessed toward a vertically lower side with the gear housing 3 mounted on the vehicle. A transmission-side unit 30 of a water detection system is provided in the recessed portion 3f. The water detection system detects water leaked into the gear housing 3. Details of the water detection system will be described below. The transmission-side unit 30 is fixed to the gear housing 3 by being sandwiched between the first gear housing portion 3a and the second gear housing portion 3b on the joint surface A. This fixing can prevent or reduce detachment of the transmission-side unit 30. An inclined surface 3g is formed on each of vertically lower portions of inner walls of the first gear housing portion 3a and the second gear housing portion 3b with the gear housing 3 mounted on the vehicle. The inclined surface 3g is formed so as to be inclined toward the vertically lower side as being getting closer to the opening portion 3e. A groove portion 3h is formed at a part of the inclined surface 3g provided at the first gear housing portion 3a. The groove portion 3h is formed so as to be recessed toward the vertically lower side and extend toward the transmission-side unit 30 side with the gear housing 3 mounted on the vehicle. In the gear housing 3, a rack bar containing portion 3d where the rack bar 6 is contained is formed so as to cylindrically extend from the ball screw mechanism containing portion 3c toward each of a right-side turning target wheel side and a left-side turning target wheel side.

The ball screw mechanism 20 is a speed reducer that transmits a rotational force of the electric motor 4 to the rack bar 6. The ball screw mechanism 20 includes a wheel turning shaft-side ball screw groove 21, a nut 22, a nut-side ball screw groove 23, balls 24, and a tube 25. The wheel turning shaft-side ball screw groove 21 is a helical groove provided on the outer peripheral side of the rack bar 6. The nut 22 is provided so as to surround the rack bar 6. The nut 22 is annularly formed with use of a steel material. The nut 22 is supported so as to be able to rotate and unable to be axially displaced relative to the gear housing 3. An output pulley 26 is fixed to an outer periphery of the nut 22. The output pulley 26 is formed cylindrically so as to surround the rack bar 6. The output pulley 26 rotates according to a rotation of the nut 22. A belt (a transmission member) 27 is hung on the output pulley 26. The belt 27 transmits a rotation of the input pulley 14 to the output pulley 26. Assuming that a rotational axis of the nut 22 is a first reference axis line L1, a second reference axis line L2 corresponding to a rotational axis of the input pulley 14 is radially offset from the first reference axis line L1. The nut-side ball screw groove 23 is a helical groove formed on an inner periphery of the nut 22. The nut-side ball screw groove 23 forms a ball circulation groove 26 together with the wheel turning shaft-side ball screw groove 21. A plurality of balls 24 is loaded in the ball circulation groove 26. The balls 24 are formed with use of a steel material. The tube 25 is provided on the outer peripheral side of the nut 22, and the balls 24 after reaching one end side or the other end side of the ball circulation groove 26 are returned to the other end side or the one end side of the ball circulation groove 26 via the tube 25. The ball screw mechanism 20 works in such a manner that the plurality of balls 24 is displaced in the ball circulation groove 26 according to the rotation of the nut 22 relative to the rack bar 6, thereby causing the rack bar 6 to be displaced relative to the nut 22 in a longitudinal direction of the rack bar 6 (the vehicle width direction).

[Water Detection System]

The electric power steering apparatus 1 according to the first embodiment includes the water detection system for detecting the water leaked into the gear housing 3. The water detection system includes the transmission-side unit 30 provided in the gear housing 3 and a reception-side unit 31 provided in the ECU housing 16.

(Transmission-Side Unit)

Figure 5:
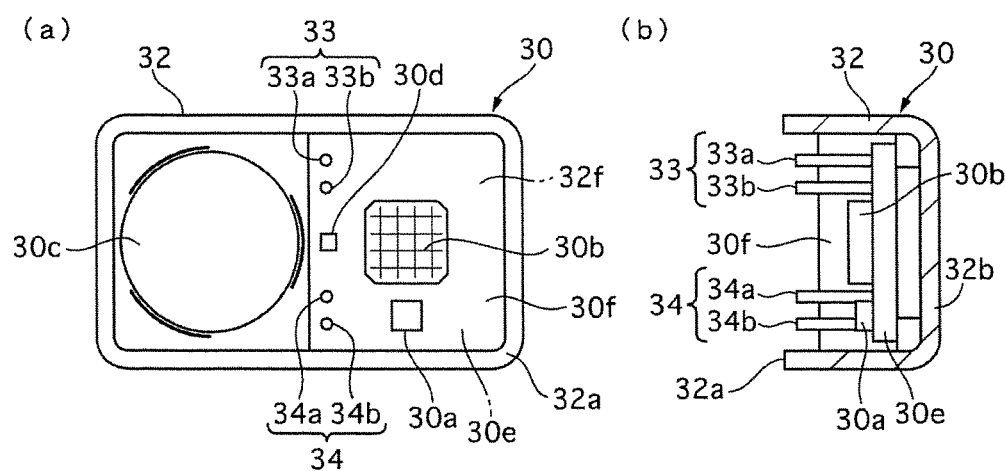
FIG. 5 illustrates a transmission-side unit 30 according to the first embodiment, and (a) and (b) show a front view and a side view, respectively.

FIGS. 5(*a*) and 5(*b*) illustrate the transmission-side unit 30 according to the first embodiment. In particular, FIGS. 5(*a*) and 5(*b*) are a front view and a side view, respectively. The transmission-side unit 30 includes a case 32, two water detection elements 33 and 34, a vibration sensor 30*a*, a transmitter 30*b*, a power source 30*c*, a microcomputer 30*d*, and a circuit substrate 30*e*. The case 32 is formed into a rectangular box shape opened on a front surface side thereof. The two water detection elements 33 and 34, the vibration sensor 30*a*, the transmitter 30*b*, the power source 30*c*, the microcomputer 30*d*, and the circuit substrate 30*e* are contained in the case 32. The first water detection element 33 includes a pair of positive and negative metallic terminals 33*a* and 33*b*. The pair of metallic terminals 33*a* and 33*b* function to detect whether there is the leak of the water by detecting a change in a resistance value between the terminals due to short-circuiting between the terminals that is caused by the water. The pair of metallic terminals 33*a* and 33*b* is disposed in proximity to each other along a direction of a short side of the case 32. The pair of metallic terminals 33*a* and 33*b* has a gold-plated surface. This configuration can prevent or reduce a detection failure accompanying oxidation of the pair of metallic terminals 33*a* and 33*b* due to water vapor in an atmosphere. Distal ends of the pair of metallic terminals 33*a* and 33*b* are positioned closer to a bottom surface 32*b* side of the case 32 with respect to an opening end 32*a* of the case 32. The second water detection element 34 is also similarly configured, and includes a pair of positive and negative metallic terminals 34*a* and 34*b* having a gold-plated surface. The vibration sensor 30*a* detects a level of a vibration of the vehicle body. The vibration sensor 30*a* according to the first embodiment is set to a resonant frequency capable of realizing detection of a vibration when the engine of the vehicle is started. The transmitter 30*b* wirelessly transmits output signals of the two water detection elements 33 and 34 (the resistance value between the terminals). The provision of the two sets of water detection elements allows, even when a failure has occurred in one of them, the detection to continue with use of the other of them. The power source 30*c* supplies power to the two water detection elements 33 and 34, the vibration sensor 30*a*, and the transmitter 30*b*. In the first embodiment, a battery is used as the power source 30*c*. This configuration allows the transmission-side unit 30 to complete the power supply to the two water detection elements 33 and 34, the vibration sensor 30*a*, and the transmitter 30*b* in itself. While the power is constantly supplied from the power source 30*c* to the vibration sensor 30*a*, the power supply to the two water detection elements 33 and 34 and the transmitter 30*b* is controlled by the microcomputer 30*d*. When the vibration is detected by the vibration sensor 30*a* at the time of the start of the engine, the microcomputer 30*d* keeps supplying the power from the power source 30*c* to the two water detection elements 33 and 34 and the transmitter 30*b* until a predetermined time period has elapsed. It should be noted that the present embodiment is constructed assuming that power consumption by the vibration sensor 30*a* is lower than power consumption by the two water detection elements 33 and 34 and the transmitter 30*b*. The transmission-side unit 30 wirelessly transmits the output signals of the two water detection elements 33 and 34 every time a predetermined time interval has elapsed (for example, every 30 minutes or every hour), since the engine of the vehicle is started until the predetermined time period has elapsed. The transmission-side unit 30 may be configured to transmit the output signals of the two water detection elements 33 and 34 only once after the engine is started. Safety can be enhanced by detecting the leak of the water when the engine is started, i.e., before the vehicle starts running.

The two water detection elements 33 and 34, the vibration sensor 30*a*, the transmitter 30*b*, and the microcomputer 30*d* are mounted on the circuit substrate 30*e*. The circuit substrate 30*e* is disposed on one of left and right sides of a longitudinal center of the case 32, and the power source 30*c* is disposed on the other of the left and right sides. The transmitter 30*b* is disposed at a generally central portion of the circuit substrate 30*e*. The vibration sensor 30*a* is disposed side by side with the transmitter 30*b* in the direction of the short side of the case 32. The two water detection elements 33 and 34 are disposed at positions between the transmitter 30*b* and the power source 30*c* in a direction of a long side of the case 32. The two water detection elements 33 and 34 are disposed along the direction of the short side of the case 32. The microcomputer 30*d* is disposed at a position between the two water detection elements 33 and 34 in the direction of the short side of the case 32. The vibration sensor 30*a*, the transmitter 30*b*, the power source 30*c*, the microcomputer 30*d*, and the circuit substrate 30*e* are covered with a potting layer (a resin potting layer) 30*f* for waterproofing in the case 32. The distal end of each of the metallic terminals 33*a*, 33*b*, 34*a*, and 34*b* of the two water detection elements 33 and 34 protrudes beyond a surface of the potting layer 30*f* toward the opening end 32*a* side of the case 32. The transmission-side unit 30 is provided in the recessed portion 3*f* of the first gear housing portion 3*a* while the opening end 32*a* side of the case 32 faces vertically upward, and the direction of the short side of the case 32 faces in the longitudinal direction of the rack bar 6 with the gear housing 3 mounted on the vehicle. Therefore, the two water detection elements 33 and 34 are positioned at a vertically lowermost portion inside the gear housing 3 with the gear housing 3 mounted on the vehicle. The water leaked into the gear housing 3 will flow toward the vertically lower side along the inclined surface 3*g* due to the force of gravity, and be pooled in the recessed portion 3*f* provided at the lowermost portion of the gear housing 3. Therefore, the two water detection elements 33 and 34 are disposed at the lowermost portion, which allows them to efficiently detect the water. Further, the leaked water can be efficiently collected due to the inclined surface 3*g*. The inclined surface 3*g* can be realized by utilizing a draft angle of a mold in the casting. Further, the inclined surface 3*g* is provided with the groove portion 3*h* extending toward the transmission-side unit 30, which allows the water to be collected around the transmission-side unit 30 by running along the groove portion 3h, thereby allowing the water to be efficiently detected. Further, the transmission-side unit 30 is provided in the recessed portion 3f where the water is pooled, which allows the water to be efficiently detected.

(Reception-Side Unit)

The reception-side unit 31 includes a receiver 31a and a determination circuit 31b. The receiver 31a and the determination circuit 31b are mounted on the circuit substrate 15b. The receiver 31a and the determination circuit 31b are disposed in proximity to the connector portion 19. The receiver 31a receives the output signals of the two water detection elements 33 and 34 that are wirelessly transmitted from the transmitter 30b. The determination circuit 31b determines whether there is the leak of the water into the gear housing 3, based on the output signals received by the receiver 31a. When the water causes the short-circuiting between the pair of metallic terminals 33a and 33b, the resistance value between the terminals reduces compared to before the short-circuiting occurs. The same also applies to the resistance value between the pair of metallic terminals 34a and 34b. Therefore, it can be determined that the water is leaked into the gear housing 3 if the resistance value between the terminals on at least one of the two water detection elements 33 and 34 reduces to a predetermined determination threshold value or lower.

When detecting that the water is leaked into the gear housing 3 by the determination circuit 31b, the microcomputer 30d warns a driver with a display, a sound, and/or the like, and prompts the driver to conduct an inspection and/or a repair.

(Prevention or Reduction of Complication of Apparatus)

Electric power steering apparatuses using the metallic ball screw mechanism as the speed reducer may be subject to generation of rust and thus a reduction of work efficiency when water is leaked into the gear housing due to a breakage of the dust boot or the like. Therefore, the electric power steering apparatuses using the ball screw mechanism are more largely affected by the rust and raises a high requirement for water detection compared to power steering apparatuses using a resin worm gear as the speed reducer. The conventional electric power steering apparatuses connect, via wired communication, the water detection element and the determination circuit spaced apart from each other while being respectively positioned inside and outside the gear housing, and transmit the output signal of the water detection element to the determination circuit, thereby resulting in the complication of the apparatus.

Therefore, in the first embodiment, the water detection system includes the transmission-side unit 30 provided in the gear housing 3 and including the two water detection elements 33 and 34, and the reception-side unit 31 provided in the ECU housing 16 and including the determination circuit 31b. The transmission-side unit 30 wirelessly transmits the output signals of the two water detection elements 33 and 34, and the reception-side unit 31 receives the output signals wirelessly transmitted from the transmission-side unit 30. Wirelessly transmitting and receiving the signals can realize omission of a wiring connecting the water detection elements 33 and 34 and the determination circuit 31b to each other. This configuration can prevent or reduce the complication of the apparatus compared to the configuration that transmits the signals via wired communication in a case where the two water detection elements 33 and 34 and the determination circuit 31 should be positioned separately from each other.

Then, the gear housing 3 and the ECU housing 16 are made from the aluminum alloy, and therefore exhibit a high radio-wave cutoff performance. Further, the electric motor 4, which becomes a noise source, is provided in the motor housing 13 in communication with the inside of the gear housing 3. This raises a necessity of securing a path of the wireless signal to allow the wireless signal to be reliably received by the reception-side unit 31 side, i.e., a path of the wireless signal that is not closed by aluminum and is less affected by the noise source. In the first embodiment, the dust boots 11 and 11 covering the opening portions 3i and 3i of the gear housing 3 and the connector portion 19 exposed to outside the ECU housing main body portion 17 are used as the path of the wireless signal. The dust boots 11 and 11 and the connector portion 19 are made from the synthetic resin, and therefore exhibit a high radio-wave transmittance. In addition, this path is isolated from the electric motor 4 that becomes the noise source via the motor housing 13. This configuration allows the wireless signal to be reliably received by the reception-side unit 31 side. Further, the reception-side unit 31 is provided in proximity to the connector portion 19 made from the synthetic resin, which eliminates a necessity of additionally providing a resin portion for the reception-side unit 31.

The first embodiment brings about the following advantageous effects.

(1-1) The water detection system, which is configured to detect the leak of the water into the apparatus mounted on the vehicle (the electric power steering apparatus 1), includes the transmission-side unit 30 provided in the apparatus mounted on the vehicle. The transmission-side unit 30 includes the water detection elements 33 and 34 configured to detect the water, the transmitter 33b configured to wirelessly transmit the output signals of the water detection elements 33 and 34, and the power source 30c configured to supply the power to the water detection elements 33 and 34 and the transmitter 30b. Further, the water detection system includes the reception-side unit 31 spaced apart from the transmission-side unit 30. The reception-side unit 31 includes the receiver 31a configured to receive the output signals wirelessly transmitted from the transmitter 30b, and the determination circuit 31b configured to determine whether there is the leak of the water into the apparatus mounted on the vehicle, based on the output signals received by the receiver 31a.

Therefore, in the case where the water detection elements 33 and 34 and the determination circuit 13b should be positioned separately from each other, the first embodiment can prevent or reduce the complication of the apparatus compared to the configuration that transmits the signal via wired communication.

(2-2) In the water detection system described in (1-1), the transmission-side unit 30 includes the vibration sensor 30a configured to detect the vibration, and the power is supplied from the power source 30c to the water detection elements 33 and 34 and the transmitter 30b only when the vibration sensor 30c detects the vibration.

The power is supplied to the water detection elements 33 and 34 or the transmitter 30b only when the vibration sensor 30c detects the vibration, such as when the door of the vehicle is opened or closed by the driver, a starter is driven, and the engine is driven, so that the first embodiment can reduce the power consumption.

(3-9) In the water detection system described in (1-1), the transmission-side unit 30 detects the leak of the water into the electric power steering apparatus 1 of the vehicle. The electric power steering apparatus 1 includes the steering mechanism 2 configured to turn the turning target wheel according to the rotation of the steering wheel, the metallic gear housing 3 containing the steering mechanism 2 therein, and the electric motor 4 configured to provide the steering force to the steering mechanism 2. The transmission-side unit 30 is provided in the gear housing 3. The driving of the electric motor 4 is controlled by the controller 15 including the microcomputer 15a mounted thereon. The controller 15 includes the ECU housing 16 containing the microcomputer 15a therein, and the connector portion 19 provided at the ECU housing 16 and configured to receive the signal on the vehicle side via wired communication. The reception-side unit 31 is provided in the ECU housing 16.

The leak of the water into the gear housing 3 of the electric power steering apparatus 1 may cause an abnormality on an internal member, such as rust generated thereon and a foreign object bitten thereby, so that the first embodiment can enhance the safety of the steering due to the provision of the water detection system at the electric power steering apparatus 1.

(4-10) In the water detection system described in (3-9), the gear housing 3 includes the communication passage (the opening portions 3i and 3i) establishing communication between inside and outside the gear housing 3.

The first embodiment allows the wireless signals to be reliably transmitted due to the provision of the openings not closed by the metallic member at the gear housing 3.

(5-12) In the water detection system described in (3-9), the gear housing 3 includes the first gear housing portion 3a and the second gear housing portion 3b jointed to the first gear housing portion 3a. The transmission-side unit 30 is provided in proximity to the joint surface A where the first gear housing portion 3a and the second gear housing portion 3b are jointed to each other.

The joint surface A serves as the opening portion leading to inside the gear housing 3, and therefore the first embodiment facilitates installation of the transmission-side unit 30.

(6-17) In the water detection system described in (3-9), the ECU housing 16 includes the ECU housing main body portion 17 made from the metallic material, and the resin portion (the connector portion 19) made from the resin material and provided so as to be exposed to outside the ECU housing 16. The reception-side unit 31 is provided in proximity to the resin portion.

The reception-side unit 31 is provided in proximity to the resin portion that allows the wireless signals to easily pass therethrough, so that the first embodiment can improve accuracy of the reception of the wireless signals.

(7-21) In the water detection system described in (3-9), the electric power steering apparatus 1 includes the steering shaft 5 configured to transmit the rotation of the steering wheel, the pinion gear 8a provided at the steering shaft 5, the rack bar 6 including the rack gear 6a meshed with the pinion gear 8a and configured to covert the rotation of the pinion gear 8a rotatable according to the rotation of the steering shaft 5 into the axial movement, and the ball screw mechanism 20 provided between the rack bar 6 and the electric motor 4 and serving as the speed reducer configured to transmit the rotational force of the electric motor 4 to the rack bar 6. The ball screw mechanism 20 includes the wheel turning shaft-side ball screw groove 21 provided on the outer peripheral side of the rack bar 6 and having the helically grooved shape, the nut 22 provided annularly so as to surround the rack bar 6 and configured in such a manner that the rotational force of the electric motor 4 is transmitted thereto, the nut-side ball screw groove 23 provided on the inner peripheral side of the nut 2, having the helically grooved shape, and forming the ball circulation groove 26 together with the wheel turning shaft-side ball screw groove 21, and the plurality of balls 24 loaded in the ball circulation groove 26. The plurality of balls 24 is displaced in the ball circulation groove 26 according to the rotation of the nut 22 relative to the rack bar 6, thereby causing the rack bar 6 to be displaced in the longitudinal direction of the rack bar 6 relative to the nut 22.

The electric power steering apparatus 1 including the ball screw mechanism 20 as the speed reducer is especially largely affected by a problem of the rust on the speed reducer, and therefore raises a high degree of necessity for the water detection in view of the safety of the steering. Therefore, the employment of the water detection system according to the first embodiment can enhance the safety of the steering.

(8-29) The electric power steering apparatus includes the ball screw mechanism 20. The ball screw mechanism 20 includes the rack bar 6 configured to turn the turning target wheel according to the rotation of the steering wheel, the wheel turning shaft-side ball screw groove 21 provided on the outer peripheral side of the rack bar 6 and having the helically grooved shape, the nut 22 provided annularly so as to surround the rack bar 6, the nut-side ball screw groove 23 provided on the inner peripheral side of the nut 22, having the helically grooved shape, and forming the ball circulation groove 26 together with the wheel turning shaft-side ball screw groove 21, and the plurality of balls 24 loaded in the ball circulation groove 26. The ball screw mechanism 20 is configured in such a manner that the plurality of balls 24 is displaced in the ball circulation groove 26 according to the rotation of the nut 22 relative to the rack bar 6, thereby causing the rack bar 6 to be displaced in the longitudinal direction of the rack bar 6 relative to the nut 22. The electric power steering apparatus further includes the output pulley 26 formed cylindrically so as to surround the rack bar 6 and configured to rotate according to the rotation of the nut 22, and the input pulley 14 disposed in such a manner that the second reference axis line L2 corresponding to the rotational axis is radially offset from the first reference axis line L1 that is the rotational axis of the nut 22. The input pulley 14 is cylindrically formed. The electric power steering apparatus 1 further includes the belt 27 provided so as to extend between the output pulley 26 and the input pulley 14 and configured to transmit the rotation of the input pulley 14 to the output pulley 26, the electric motor 4 configured to rotationally drive the input pulley 14, the gear housing 3 made from the metallic material and containing at least a part of the ball screw mechanism 20 and the rack bar 6, the controller 15 spaced apart from the electric motor 4 and configured to control the driving of the electric motor 4, and the transmission-side unit 30 provided in the gear housing 3. The transmission-side unit 30 includes the water detection elements 33 and 34 configured to detect the water, the transmitter 30b configured to wirelessly transmit the output signals of the water detection element 33 and 34, and the power source 30c configured to supply the power to the water detection elements 33 and 34 and the transmitter 30c. The electric power steering apparatus 1 further includes the reception-side unit 31 provided in the controller 15. The reception-side unit 31 includes the receiver 31a configured to receive the output signals wirelessly transmitted from the transmitter 30b, and the determination circuit 31b configured to determine whether there is the leak of the water into the gear housing 3, based on the output signals received by the receiver 31a.

Therefore, in the case where the water detection elements 33 and 34 and the determination circuit 13b should be positioned separately from each other, the first embodiment can prevent or reduce the complication of the apparatus compared to the configuration that transmits the signal via wired communication.

Second Embodiment

A second embodiment is different from the first embodiment in terms of the transmission-side unit provided on the gear housing so as to be detachably attachable. Similar portions to the first embodiment will be identified by the same reference numerals, and will not be illustrated and redundantly described below.

Figure 6:
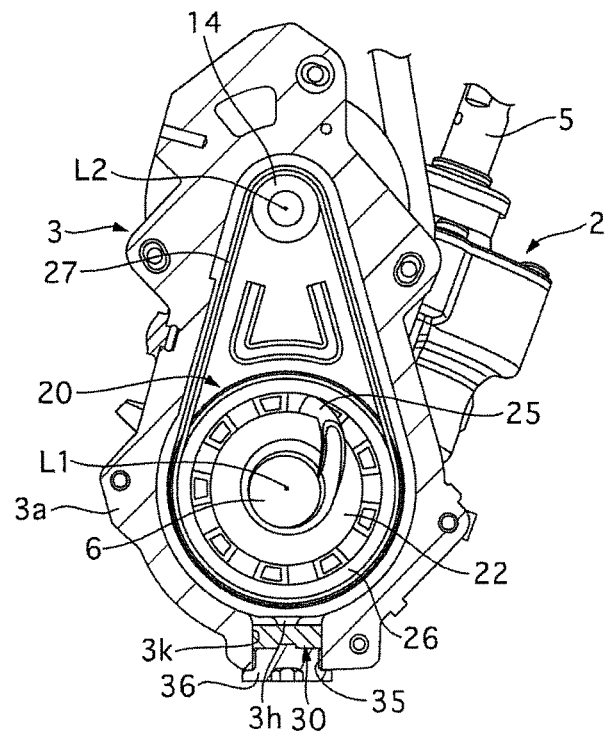
FIG. 6 is a cross-sectional view of the steering mechanism 2 of the gear housing 3 according to a second embodiment.

FIG. 6 is a cross-sectional view of the steering mechanism 2 of the gear housing 3 according to the second embodiment. A through-hole 35 is provided on a vertically below the transmission-side unit 30 in the first gear housing portion 3a, i.e., at a bottom side of the recessed portion 3f with the gear housing 3 mounted on the vehicle. The through-hole 35 is formed so as to allow the transmission-side unit 30 to be inserted therethrough. The through-hole 35 is closed by a plug 36. The plug 36 is made from aluminum alloy similarly to the gear housing 3. The plug 36 is threadably engaged with the through-hole 35 from outside the gear housing 3, and can be attached and detached from outside with use of a tool.

In the second embodiment, a power generation element is used as the power source 30c of the transmission-side unit 30. The power generation element generates power with the aid of a vibration due to the running of the vehicle, so that the second embodiment can reduce a risk that the battery may run out.

In the second embodiment, the vibration sensor 30a of the transmission-side unit 30 is set to a resonant frequency that can achieve detection of a vibration generated when a door is opened or closed or the driver gets in or off the vehicle. If the vibration is detected by the vibration sensor 30a when the door is opened or closed or the driver gets in or off the vehicle, the microcomputer 30d keeps supplying the power from the power source 30c to the two water detection elements 33 and 34 and the transmitter 30b by a similar manner to the first embodiment until a predetermined time period has elapsed. The vibration sensor 30a can detect that the door is opened or closed or the driver gets in or off the vehicle before the engine is started, so that the water detection system can early take safety measures such as the detection of the water, the determination about the leak of the water, and the issue of the warning to the driver. Further, the water detection system can take safety measures before the vehicle starts running even in a case of an electric vehicle or a hybrid vehicle where no vibration occurs due to the start of the engine when the vehicle starts running.

Further, in the second embodiment, the cover member 18 closing the ECU housing main body opening portion 17a is formed with use of a synthetic resin material. The reception-side unit 31 is provided in proximity to the cover member 18, which allows the cover member 18 to be used as the path of the wireless signal.

The second embodiment brings about the following advantageous effects.

(9-16) In the water detection system described in (3-9), the gear housing 3 includes the through-hole 35 formed so as to establish the communication between inside and outside the gear housing 3. The transmission-side unit 30 is provided so as to be detachably attachable from outside the gear housing 3 via the through-hole 35.

Therefore, the transmission-side unit 30 can be attached and detached without disassembling the gear housing 3, which facilitates, for example, replacement of the battery and a repair of the transmission-side unit 30.

Third Embodiment

A third embodiment is different from the first embodiment in terms of the reception-side unit provided in the torque sensor housing. Similar portions to the first embodiment will be identified by the same reference numerals, and will not be illustrated and redundantly described below.

Figure 7:
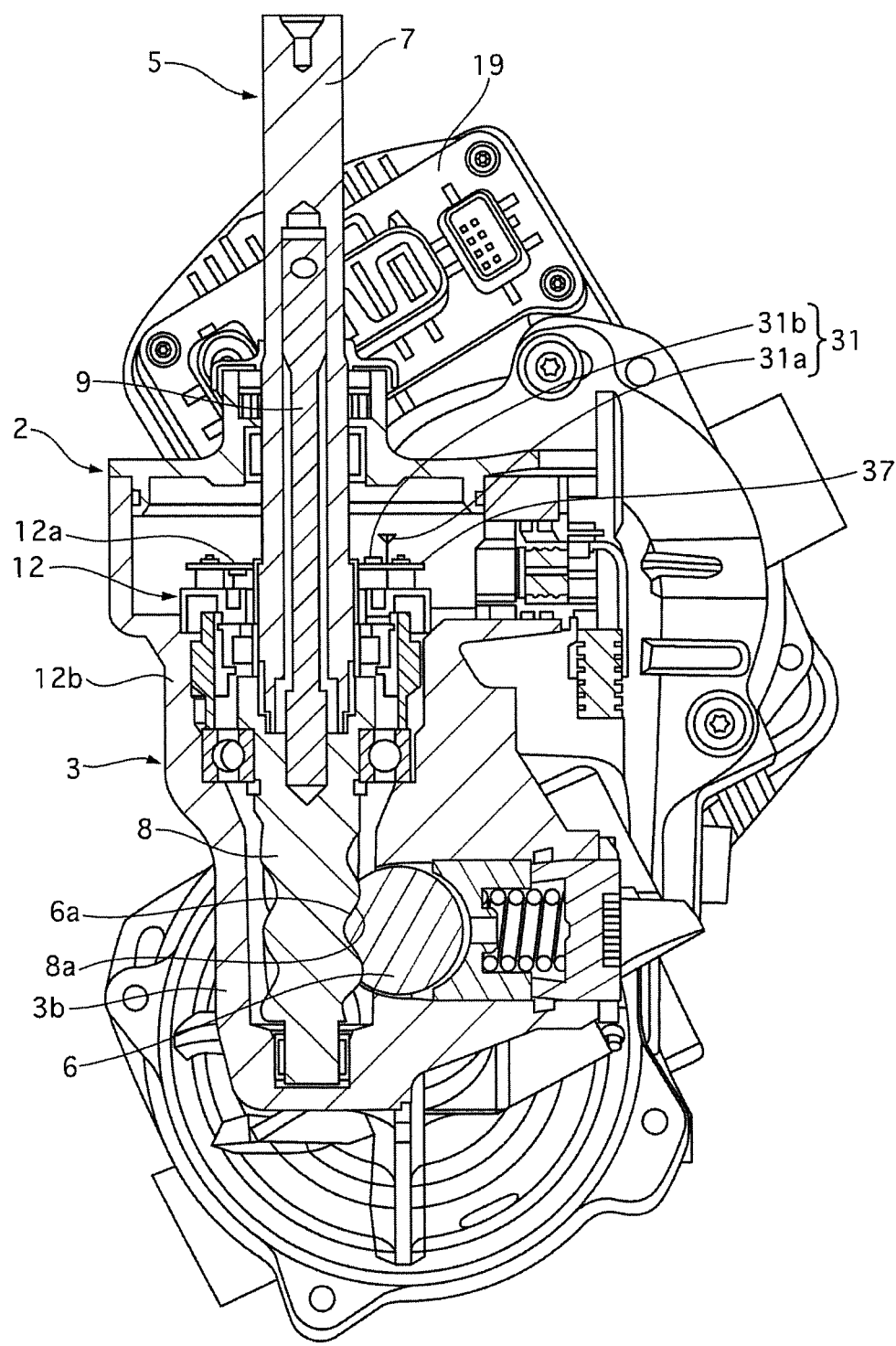
FIG. 7 is a cross-sectional view of the steering mechanism 2 of the gear housing 3 according to a third embodiment.

FIG. 7 is a cross-sectional view of the steering mechanism 2 of the gear housing 3 according to the third embodiment. The reception-side unit 31 according to the third embodiment is provided in the sensor housing 12b of the torque sensor 12. The receiver 31a and the determination circuit 31b forming the reception-side unit 31 is mounted on a circuit substrate 37 provided in the sensor housing 12b. A result of the determination about whether there is the leak of the water that is yielded by the determination circuit 31b is input to the microcomputer 30d of the controller 15 via the signal system harness and the bus bar together with the output signal of the torque sensor 12.

The insides of the gear housing 3 and the sensor housing 12b are not closed by the aluminum alloy having the high radio-wave cutoff performance and also free from the noise source between the transmission-side unit 30 and the reception-side unit 31. Therefore, the wireless signal output from the transmission-side unit 30 can be reliably received by the reception-side unit 31. Further, the third embodiment can reduce the distance between the transmission-side unit 30 and the reception-side unit 31 compared to the configuration in which the reception-side unit 31 is disposed in the ECU housing 16.

Fourth Embodiment

A fourth embodiment is different from the first embodiment in terms of the transmission unit provided at a position that is closer to the end of the rack bar containing portion than the ball screw mechanism containing portion in the gear housing. Similar portions to the first embodiment will be identified by the same reference numerals, and will not be illustrated and redundantly described below.

Figure 8:
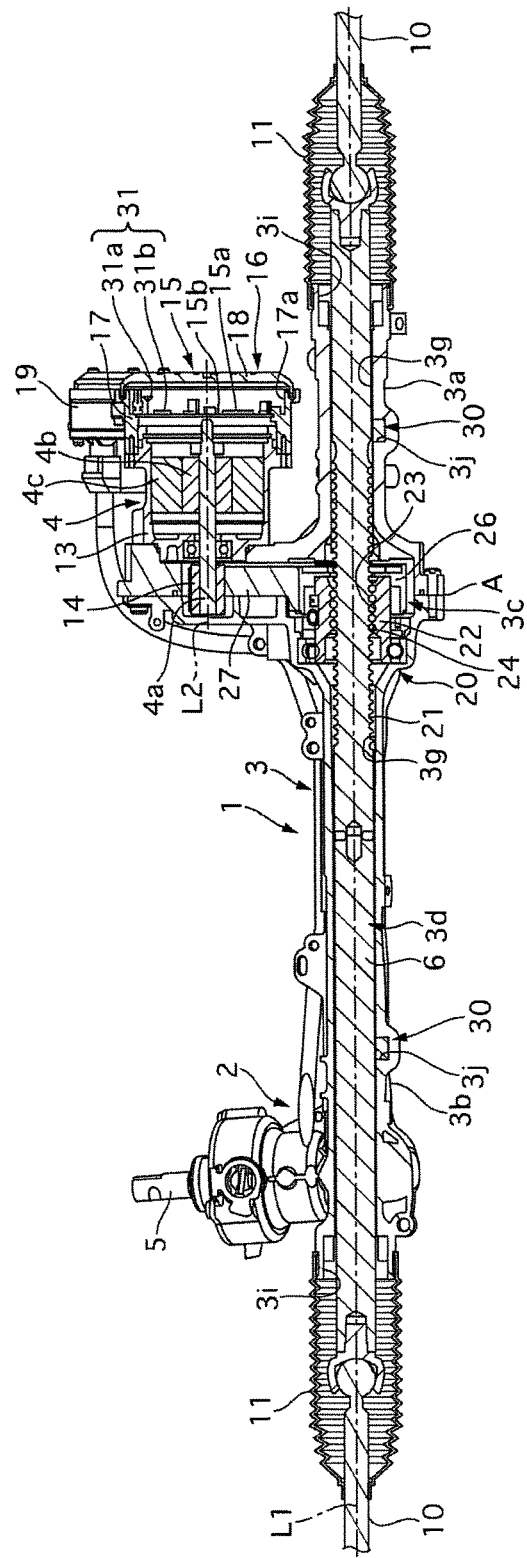
FIG. 8 is a front view partially including a cross-sectional view that illustrates the electric power steering apparatus 1 according to a fourth embodiment.

FIG. 8 is a front view partially including a cross-sectional view that illustrates the electric power steering apparatus 1 according to the fourth embodiment. In the fourth embodiment, transmission-side units 30 are provided between the ball screw mechanism containing portion 3c and the pair of ends of the rack bar containing portion 3d, respectively. The two transmission-side units 30 and 30 are provided in recessed portions 3j and 3j formed at the rack bar containing portion 3d, respectively.

The receiver 31a of the reception-side unit 31 receives output signals from the four water detection elements 33 and 34 that are wirelessly transmitted from the respective transmitters 30b. The determination circuit 31b determines that the water is leaked into the gear housing 3 if the resistance value between the terminals on at least one of the four water detection elements 33 and 34 reduces to a predetermined determination threshold value or lower.

The leak of the water into the gear housing 3 is often caused by a breakage of the dust boot 11 made from the synthetic resin, and the water travels from the end side of the rack bar containing portion 3d to the ball screw mechanism containing portion 3c, so that positioning the transmission-side unit 30 at the position that is closer to the end side of the rack bar containing portion 3d than the ball screw mechanism 20 allows the water to be detected before reaching the ball screw mechanism 20. Therefore, the fourth embodiment allows the leak of the water to be detected early and prevent the generation of the rust on the ball screw mechanism 20 in advance.

Fifth Embodiment

A fifth embodiment is different from the first embodiment in terms of the transmission unit provided in a region surrounded by the input pulley, the output pulley, and the belt. Similar portions to the first embodiment will be identified by the same reference numerals, and will not be illustrated and redundantly described below.

Figure 9:
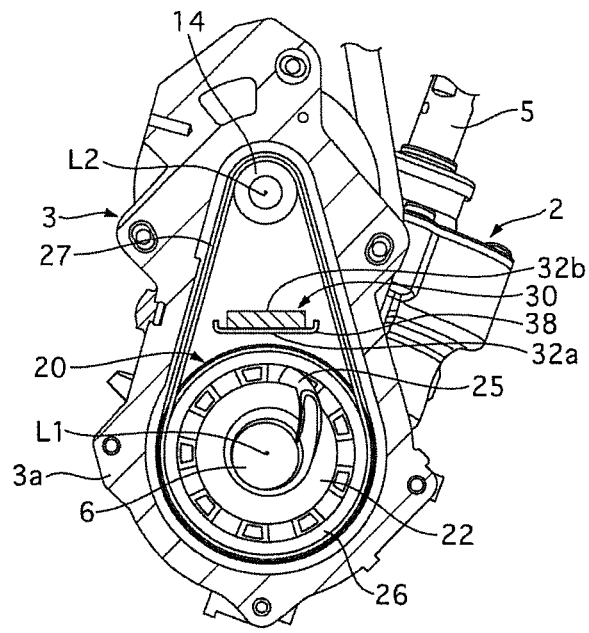
FIG. 9 is a cross-sectional view of the steering mechanism 2 of the gear housing 3 according to a fifth embodiment.

FIG. 9 is a cross-sectional view of the steering mechanism 2 of the gear housing 3 according to the fifth embodiment. The transmission-side unit 30 according to the fifth embodiment is provided in the region surrounded by the input pulley 14, the output pulley 26, and the belt 27 on a plane perpendicular to the rotational axis of the nut 22 (the first reference axis line L1) in the first gear housing portion 3a. The transmission-side unit 30 is positioned vertically above the ball screw mechanism 20 with the gear housing 3 mounted on the vehicle. The transmission-side unit 30 is fixed on a unit support portion 38 provided at the first gear housing 3a while the opening end 32a of the case 32 faces vertically downward and the direction of the short side of the case 32 faces in the longitudinal direction of the rack bar 6. A plurality of cutouts (not illustrated) is formed on the opening end 32a side of the case 32. The plurality of cutouts allow the water to be leaked into the case 32. Now, the distal end of each of the metallic terminals 33a, 33b, 34a, and 34b is positioned on the bottom surface 32b side of the case 32 with respect to the opening end 32a of the case 32. Therefore, while the opening end 32a of the case 32 is in abutment with the unit support portion 38, the distal end of each of the metallic terminals 33a, 33b, 34a, and 34b is spared apart from the unit support portion 38. In other words, the opening end 32a of the case 32 functions as a regulation portion that regulates a displacement of the two water detection elements 33 and 34 toward the facing surface side (the unit support portion 38 side). This configuration can prevent or reduce a breakage of the water detection elements 33 and 34 and false detection due to short-circuiting between the positive-side metallic terminals 33a and 34a and the negative-side metallic terminals 33b and 34b.

In the fifth embodiment, the water leaked into the ball screw mechanism containing portion 3c of the gear housing 3 is scooped up from the lowermost portion of the ball screw mechanism containing portion 3c by the output pulley 26 to be splashed vertically upward. As a result, the water is attached to the transmission-side unit 30 and the unit support portion 38 disposed vertically above the output pulley 26. A part of the attached water is leaked into the case 32 via the cutouts of the case 32, so that the leak of the water can be detected by the two water detection elements 33 and 34. Conventionally, the region surrounded by the input pulley 14, the output pulley 26, and the belt 27 has been a dead space in the gear housing 3. The dead space can be utilized by placing the transmission-side unit 30 in the above-described region Sixth Embodiment A sixth embodiment is different from the first embodiment in terms of the transmission-side unit provided outside the belt. Similar portions to the first embodiment will be identified by the same reference numerals, and will not be illustrated and redundantly described below.

Figure 10:
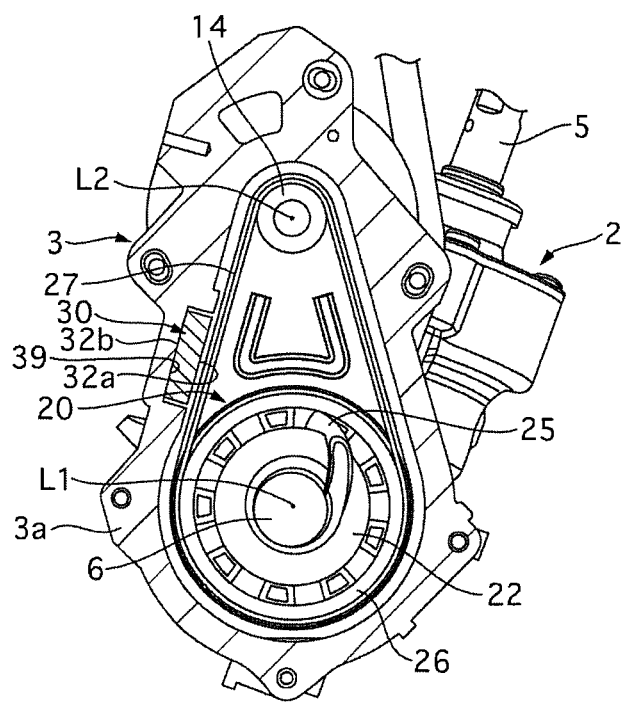
FIG. 10 is a cross-sectional view of the steering mechanism 2 of the gear housing 3 according to a sixth embodiment.

FIG. 10 is a cross-sectional view of the steering mechanism 2 of the gear housing 3 according to the sixth embodiment. The transmission-side unit 30 according to the sixth embodiment is provided outside the belt 27 on the plane perpendicular to the rotational axis of the nut 22 (the first reference axis line L1) in the first gear housing 3a. The transmission-side unit 30 is provided in a recessed portion 39 formed at the first gear housing portion 3a while the opening end 32a of the case 32 faces toward the belt 27 side.

Figure 11:
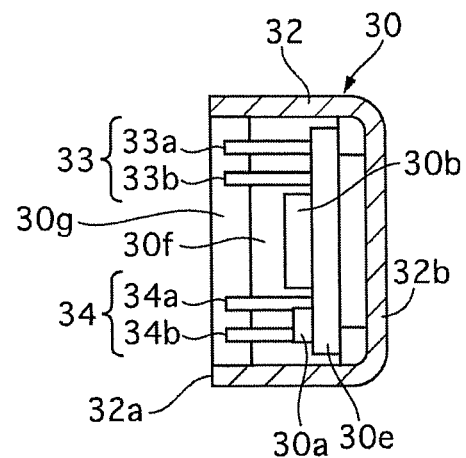
FIG. 11 is a side view of the transmission-side unit 30 according to the sixth embodiment.

FIG. 11 is a side view of the transmission-side unit 30 according to the sixth embodiment. The transmission-side unit 30 according to the sixth embodiment includes a sponge 30g as a water absorber attached to a surface of the potting layer 30f in the case 32. The sponge 30g is provided in such a manner that a surface thereof is located on the same plane as the opening end 32a of the case 32.

In the sixth embodiment, the water leaked into the ball screw mechanism containing portion 3c of the gear housing 3 is splashed due to a centrifugal force of the belt 27 after being attached to the belt 27 at the lowermost portion of the ball screw mechanism 20. As a result, the sponge 30g of the transmission-side unit 30 disposed outside the belt 27 absorbs the water, so that the leak of the water can be detected by the two water detection elements 33 and 34. Further, the sponge 30g can hold the attached water for a long time period, which can improve accuracy of the detection of the water.

Seventh Embodiment

A seventh embodiment is different from the first embodiment in terms of provision of a conductivity addition substance in the gear housing. Similar portions to the first embodiment will be identified by the same reference numerals, and will not be illustrated and redundantly described below.

Figure 12:
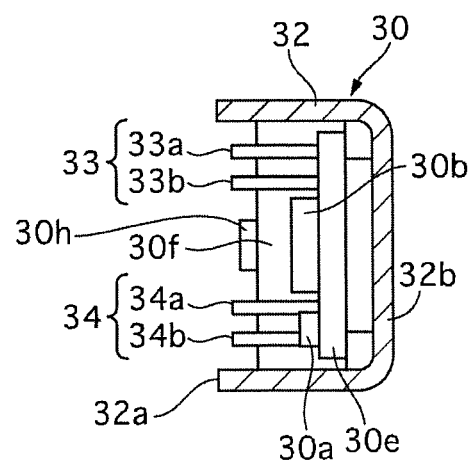
FIG. 12 is a side view of the transmission-side unit 30 according to a seventh embodiment.

FIG. 12 is a side view of the transmission-side unit 30 according to the seventh embodiment. In the transmission-side unit 30 according to the seventh embodiment, an electrolyte 30h such as salt as the conductivity addition substance is fixed to the surface of the potting layer 30f. The electrolyte 30h is melted in the water leaked into the ball screw mechanism containing portion 3c, thereby increasing conductivity of this water. If the leaked water has high purity, this may reduce the accuracy of the detection of the water by the two water detection elements 33 and 34. On the other hand, due to the provision of the electrolyte 30h that increases the conductivity of the water on the way along the path of the water, the conductivity of the water is increased when the water reaches the water detection elements 33 and 34, which can improve the accuracy of the detection of the water.

Eighth Embodiment

An eighth embodiment is different from the first embodiment in terms of provision of a water holding portion for holding the water in proximity to the transmission-side unit. Similar portions to the first embodiment will be identified by the same reference numerals, and will not be illustrated and redundantly described below.

Figure 13:
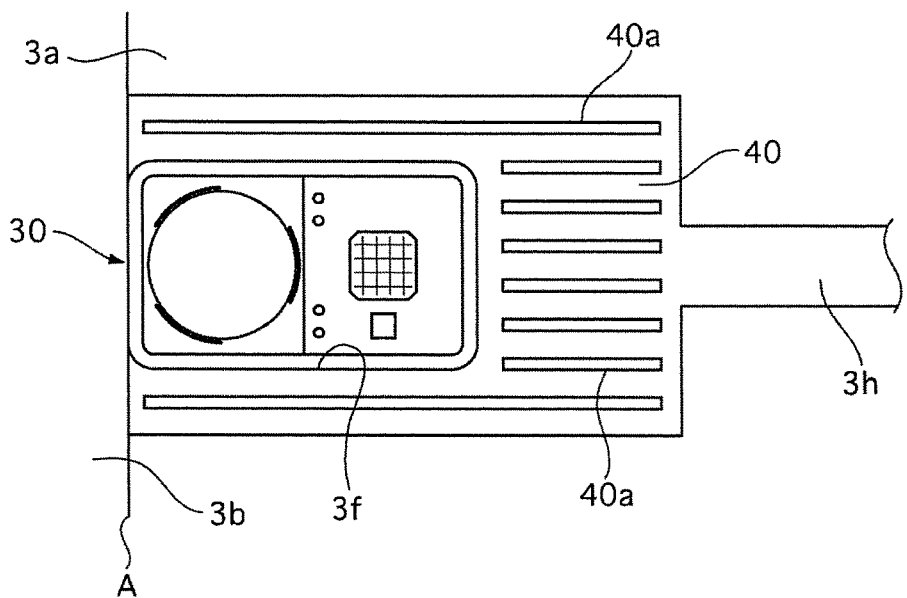
FIG. 13 is a schematic plan view illustrating main portions of the gear housing 3 according to an eighth embodiment.

FIG. 13 is a schematic plan view illustrating main portions of the gear housing 3 according to the eighth embodiment. The first gear housing portion 3a according to the eighth embodiment include a water holding portion 40 provided around the recessed portion 3f in which the transmission-side unit 30 is provided. The water holding portion 40 is located on the same plane as the opening end 32a of the case 32 in the vertical direction with the gear housing 3 mounted on the vehicle. A plurality of protruding portions 40a is provided at the water holding portion 40. The protruding portions 40a extend in the longitudinal direction of the rack bar 6. The protruding portions 40a are formed so as to protrude vertically upward with the gear housing 3 mounted on the vehicle.

The water leaked into the ball screw mechanism containing portion 3c is pooled on the surface of the potting layer 30f of the transmission-side unit 30 and in a space generated as a gap between the protruding portions 40a and 40a adjacent to each other in the water holding portion 40. Then, the gap between the adjacent protruding portions 40a and 40a is sufficiently narrow, so that the eighth embodiment can prevent or reduce, with the aid of an effect of a surface tension, an outflow of the water from the water holding portion 40 due to a vibration generated when the engine is started or the vehicle runs. In other words, instead of such a smooth surface that the water flows on a surface thereof, the water holding portion 40 configured to allow the water to be held there is provided in proximity to the transmission-side unit 30, which allows the water to be efficiently detected.

Ninth Embodiment

A ninth embodiment is different from the first embodiment in terms of provision of a temperature sensor at the transmission-side unit. Similar portions to the first embodiment will be identified by the same reference numerals, and will not be illustrated and redundantly described below.

Figure 14:
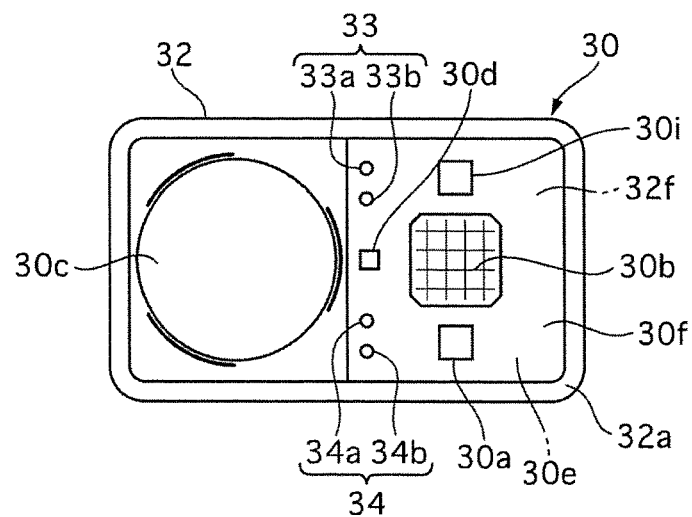
FIG. 14 is a front view of the transmission-side unit 30 according to a ninth embodiment.

FIG. 14 is a front view of the transmission-side unit 30 according to the ninth embodiment. The transmission-side unit 30 according to the ninth embodiment includes a temperature sensor 30i. The temperature sensor 30i detects an ambient temperature. The temperature sensor 30i is mounted on the circuit substrate 30e. The transmitter 30b wirelessly transmits an output signal of the temperature sensor 30i. The power source 30c supplies power to the temperature sensor 30i. The microcomputer 30d supplies the power to the temperature sensor 30i at a same timing as the power supply to the two water detection elements 33 and 34 and the transmitter 30b.

In the reception-side unit 31, the determination circuit 31b determines that the water leaked into the ball screw mechanism containing portion 3c is frozen if the resistance value between the terminals on at least one of the two water detection elements 33 and 34 is a predetermined determination threshold value or lower and, further, the temperature detected by the temperature sensor 30i is a predetermined freezing determination threshold value or lower. When the water is determined to be frozen, the microcomputer 30d outputs a request prohibiting the start of the engine to an engine controller and also notifies the user that the vehicle cannot be driven. The freezing of the water pooled in the ball screw mechanism containing portion 3c may cause immobility between the belt and the pulley and/or between the balls and the ball screw groove, thereby making the steering difficult. Therefore, the safety can be enhanced by prohibiting the start of the engine when the water leaked into the ball screw mechanism containing portion 3c is determined to be frozen.

Other Embodiments

Having described how the present invention can be embodied based on embodiments thereof, the specific configuration of the present invention is not limited to the configurations described in the embodiments, and the present invention also includes a design modification and the like thereof made within a range that does not depart from the spirit of the present invention.

For example, the power may be constantly supplied from the power source to one of the water detection element and the transmitter, and the power may be supplied to the other only when the vibration sensor detects the vibration.

The sensor housing may be molded separately from the gear housing.

A chain may be used as the transmission member of the ball screw mechanism.

The position where the conductivity addition substance is disposed may be any position between the pair of opening portions of the gear housing and the transmission-side unit.

In the following description, technical ideas other than the inventions defined in the claims that are understood from the embodiments will be described.

(10-3) In the water detection system described in (2-2), the vibration sensor detects the vibration generated when the engine of the vehicle is started.

The start of the engine of the vehicle is highly likely accompanied by the running of the vehicle. When the water is leaked into the apparatus mounted on the vehicle, the apparatus mounted on the vehicle may be affected thereby, and this influence may also affect the running. Therefore, the vibration sensor detects the start of the engine, which allows, for example, the driver to be notified of the leak of the water before the vehicle starts running, and thus enhancing the safety.

(11-4) In the water detection system described in (2-2), the vibration sensor detects the vibration generated when the door of the vehicle is opened or closed or the driver gets in or off the vehicle.

The vibration sensor can detect that the door is opened or closed or the driver gets in or off the vehicle before the engine is started, so that this configuration can early take safety measures such as the detection of the water, the determination about the leak of the water, or the issue of the warning to the driver.

(12-5) In the water detection system described in (1-1), the power source is the battery.

Therefore, the transmission-side unit can complete its operation as far as the power supply within the transmission-side unit.

(13-6) In the water detection system described in (1-1), the power source is the power generation element.

Therefore, the water detection system can reduce the risk that the battery may run out, which might occur when the battery is used.

(14-7) In the water detection system described in (1-1), the water detection element includes the pair of metallic terminals, and detects the change in the resistance value between the pair of terminals due to the short-circuiting between the pair of terminals that is caused by the water. The pair of metallic terminals has the gold-plated surface.

Therefore, the water detection system can prevent or reduce the detection failure accompanying the oxidation of the pair of metallic terminals due to the water vapor in the atmosphere.

(15-8) In the water detection system described in (1-1), the water detection element includes the first water detection element and the second water detection element.

The provision of the two sets of water detection elements allows, even when a failure has occurred in one of them, the detection to continue with use of the other of them.

(16-11) In the water detection system described in (3-9), the water detection element is provided so as to be positioned at the vertically lowermost portion within the gear housing with the gear housing mounted on the vehicle.

The water leaked into the gear housing is likely pooled at the lowermost portion of the gear housing, so that this configuration allows this pooled water to be efficiently detected.

(17-13) In the water detection system described in (5-12), the transmission-side unit is provided on the first gear housing side. The first gear housing is formed by the casting and includes the opening formed by the mold so as to be opened to the joint surface where the first gear housing and the second gear housing are jointed to each other. The vertically lower portion of the inner wall of the first gear housing portion with the gear housing mounted on the vehicle has the inclined surface formed so as to be inclined toward the vertically lower side as being getting closer to the opening portion.

The water flows toward the vertically lower side along the inclined surface and then is pooled at the lowermost portion, so that this configuration allows the leaked water to be efficiently collected and the water to be detected with improved accuracy. This inclined surface can be realized by utilizing the draft angle of the mold in the casting.

(18-14) In the water detection system described in (5-12), the transmission-side unit is fixed to the gear housing by being sandwiched between the first gear housing portion and the second gear housing portion on the joint surface.

The transmission-side unit is sandwiched between the first and second gear housing portions, which can prevent the detachment of the transmission-side unit.

(19-15) In the water detection system described in (3-9), the gear housing includes the recessed portion formed so as to be recessed toward the vertically lower side with the gear housing mounted on the vehicle. The transmission-side unit is provided in the recessed portion.

The water is pooled in the recessed portion due to the force of gravity, so that this configuration allows the water to be efficiently detected.

(20-18) In the water detection system described in (6-17), the resin portion is the connector portion. The reception-side unit is provided in proximity to the connector portion.

The connector portion is made from the resin material and the reception-side unit is provided in proximity to this connector portion, which eliminates the necessity of additionally providing the resin portion for the reception-side unit.

(21-19) In the water detection system described in (6-17), the ECU housing main body portion includes the ECU housing main body opening portion formed so as to expose the inside of the ECU housing. The ECU housing includes the cover member made from the resin material and closing the ECU housing main body opening portion. The reception-side unit is provided in proximity to the cover member.

The cover member is made from the resin material and the reception-side unit is provided in proximity to this cover member, which eliminates the necessity of additionally providing the resin portion for the reception-side unit.

(22-20) In the water detection system described in (3-9), the steering mechanism includes the steering shaft configured to transmit the rotation of the steering wheel, the pinion gear provided at the steering shaft, and the rack bar meshed with the pinion gear and configured to covert the rotation of the pinion gear rotatable according to the rotation of the steering shaft into the axial movement. The electric power steering apparatus includes the torque sensor provided at the steering shaft and configured to detect the steering torque generated at the steering mechanism. The torque sensor includes the torsion bar provided at the steering shaft, the detection unit configured to detect the torsional amount of the torsion bar, and the sensor housing containing the detection unit therein. The reception-side unit is provided in the sensor housing.

Therefore, the water detection system can reduce the distance between the transmission-side unit and the reception-side unit compared to the configuration in which the reception-side unit is disposed in the ECU housing.

(23-22) In the water detection system described in (7-21), the gear housing includes the ball screw mechanism containing portion containing the ball screw mechanism therein, and the rack bar containing portion formed so as to cylindrically extend from the ball screw mechanism containing portion toward each of the right-side turning target wheel side and the left-side turning target wheel side and containing the rack bar therein. The electric power steering apparatus includes the pair of boots provided at the pair of ends of the rack bar containing portion, respectively, made from the resin material, and configured to prevent or reduce the leak of the water from outside into the gear housing. The transmission-side unit is positioned closer to any one of the pair of ends than the ball screw mechanism containing portion is.

The leak of the water into the gear housing is often caused by the breakage of the dust boot made from the resin, and the water travels from the end side of the rack bar containing portion to the ball screw mechanism containing portion, so that positioning the transmission-side unit at the position that is closer to the end side of the rack bar containing portion than the ball screw mechanism is allows the water to be detected before reaching the ball screw mechanism, thereby leading to early detection of the leak of the water.

(24-23) In the water detection system described in (7-21), the speed reducer includes the input pulley provided at the output shaft of the electric motor, the output pulley provided at the nut, and the belt or the chain serving as the transmission member provided so as to extend between the input pulley and the output pulley. The transmission-side unit is provided in the region surrounded by the input pulley, the output pulley, and the transmission member on the plane perpendicular to the rotational axis of the nut.

The above-described region is the dead space in the gear housing. This configuration leads to the utilization of the dead space by positioning the transmission-side unit there. Further, the water leaked into the ball screw mechanism containing portion can be detected by the transmission-side unit by being scooped up by the output pulley.

(25-24) In the water detection system described in (7-21), the speed reducer includes the input pulley provided at the output shaft of the electric motor, the output pulley provided at the nut, and the belt or the chain serving as the transmission member provided so as to extend between the input pulley and the output pulley. The transmission-side unit is provided outside the transmission member on the plane perpendicular to the rotational axis of the nut.

Therefore, the water splashed due to the centrifugal force after being attached to the belt or the chain serving as the transmission member can be detected by the transmission-side unit.

(26-25) In the water detection system described in (3-9), the gear housing includes the groove portion formed so as to be recessed toward the vertically lower side and formed so as to extend toward the transmission-side unit side with the gear housing mounted on the vehicle.

The water is collected around the transmission-side unit by running along the groove portion, and therefore can be efficiently detected.

(27-26) In the water detection system described in (3-9), the gear housing includes the water holding portion provided in proximity to the transmission-side unit and configured to hold the water.

Instead of such a smooth surface that the water flows on the surface thereof, the structure configured to allow the water to be held there, such as a groove and a concavity and convexity, is provided in proximity to the transmission-side unit, which allows the water to be efficiently detected.

(28-27) In the water detection system described in (3-9), the transmission-side unit includes the regulation portion formed so as to protrude beyond the water detection element toward the facing surface side of the gear housing that faces the water detection element and configured to regulate the displacement of the water detection element toward the facing surface side of the gear housing.

This configuration can prevent or reduce damage on the water detection element or false detection due to short-circuiting of the water detection element by preventing or reducing the contact between the water detection element and the gear housing.

(29-28) In the water detection system described in (3-9), the steering mechanism includes the steering shaft configured to transmit the rotation of the steering wheel, the pinion gear provided at the steering shaft, and the rack bar meshed with the pinion gear and configured to covert the rotation of the pinion gear rotatable according to the rotation of the steering shaft into the axial movement. The gear housing includes the rack bar containing portion formed so as to cylindrically extend toward each of the right-side turning target wheel side and the left-side turning target wheel side and containing the rack bar therein. The electric power steering apparatus includes the pair of boots provided at the pair of ends of the rack bar containing portion, respectively, made from the resin material, and configured to prevent or reduce the leak of the water from outside into the gear housing, and the conductivity addition substance provided in the gear housing, positioned between the pair of opening portions and the transmission-side unit, and configured to increase the conductivity of the water by being melted in the water.

If the water leaked into the gear housing has high purity, this may reduce the accuracy of the detection of the water by the water detection element. The substance that increases the conductivity of the water is provided on the way along the path of the water, so that the conductivity of the water is increased when the water reaches the water detection element, which can improve the accuracy of the detection of the water.

Having described the several embodiments of the present invention, the above-described embodiments of the present invention are intended to only facilitate the understanding of the present invention, and are not intended to limit the present invention thereto. Needless to say, the present invention can be modified or improved without departing from the spirit of the present invention, and includes equivalents thereof. Further, the individual components described in the claims and the specification can be arbitrarily combined or omitted within a range that allows them to remain capable of achieving at least a part of the above-described objects or producing at least a part of the above-described advantageous effects.

The present application claims priority to Japanese Patent Application No. 2014-254426 filed on Dec. 16, 2014. The entire disclosure of Japanese Patent Application No. 2014-254426 filed on Dec. 16, 2014 including the specification, the claims, the drawings, and the abstract is incorporated herein by reference in its entirety.

REFERENCE SIGNS LIST 1 power steering apparatus
3 gear housing
4 electric motor
6 rack bar (wheel turning shaft)
14 input pulley
15 controller
20 ball screw mechanism
21 wheel turning-side ball screw groove
22 nut
23 nut-side ball screw groove
24 ball
26 output pulley
26 ball circulation groove
26 output pulley
27 belt (transmission member)
30 transmission-side unit
30$b$ transmitter
30$c$ power source
31 reception-side unit
31$a$ receiver
31$b$ determination circuit
33 first water detection element
34 second water detection element
L1 first reference axis line
L2 second reference axis line

The invention claimed is:

1. A water detection system for detecting a leak of water into an apparatus mounted on a vehicle, the water detection system comprising:
 a transmission-side unit provided in the apparatus mounted on the vehicle, the transmission-side unit including a water detection element configured to detect the water, a transmitter configured to wirelessly transmit an output signal of the water detection element, and a power source configured to supply power to the water detection element and the transmitter;
 a reception-side unit spaced apart from the transmission-side unit, the reception-side unit including a receiver configured to receive the output signal wirelessly transmitted from the transmitter and a determination circuit configured to determine, based on the output signal received by the receiver, whether there is the leak of the water into the apparatus mounted on the vehicle.

2. The water detection system according to claim 1, wherein the transmission-side unit includes a vibration sensor configured to detect a vibration, and the power is supplied from the power source to the water detection element or the transmitter only when the vibration sensor detects the vibration.

3. The water detection system according to claim 2, wherein the vibration sensor detects a vibration generated when an engine of the vehicle is started.

4. The water detection system according to claim 2, wherein the vibration sensor detects a vibration generated when a door of the vehicle is opened or closed or a driver gets in or off the vehicle.

5. The water detection system according to claim 1, wherein the power source is a battery.

6. The water detection system according to claim 1, wherein the power source is a power generation element.

7. The water detection system according to claim 1, wherein the water detection element includes a pair of metallic terminals, and detects a change in a resistance value between the pair of terminals due to short-circuiting between the pair of terminals that is caused by the water, and
wherein the pair of metallic terminals has a gold-plated surface.

8. The water detection system according to claim 1, wherein the water detection element includes a first water detection element and a second water detection element.

9. The water detection system according to claim 1, wherein the transmission-side unit detects a leak of water into an electric power steering apparatus of the vehicle,
wherein the electric power steering apparatus includes a steering mechanism configured to turn a turning target wheel according to a rotation of a steering wheel, a metallic gear housing containing the steering mechanism therein, and an electric motor configured to provide a steering force to the steering mechanism,
wherein the transmission-side unit is provided in the gear housing,
wherein driving of the electric motor is controlled by a controller including a microcomputer mounted thereon,
wherein the controller includes an ECU housing containing the microcomputer therein, and a connector portion provided at the ECU housing and configured to receive a signal on a vehicle side via wired communication, and
wherein the reception-side unit is provided in the ECU housing.

10. The water detection system according to claim 9, wherein the gear housing includes a communication passage establishing communication between inside and outside the gear housing.

11. The water detection system according to claim 9, wherein the water detection element is provided so as to be positioned at a vertically lowermost portion within the gear housing with the gear housing mounted on the vehicle.

12. The water detection system according to claim 9, wherein the gear housing includes a first gear housing portion and a second gear housing portion joined to the first gear housing portion, and
wherein the transmission-side unit is provided in proximity to a joint surface where the first gear housing portion and the second gear housing portion are joined to each other.

13. The water detection system according to claim 12, wherein the transmission-side unit is provided on the first gear housing side, and
wherein the first gear housing is formed by casting and includes an opening formed by a mold so as to be opened to the joint surface where the first gear housing and the second gear housing are jointed to each other, and a vertically lower portion of an inner wall of the first gear housing with the gear housing mounted on the vehicle has an inclined surface formed so as to be inclined toward a vertically lower side as being getting closer to the opening portion.

14. The water detection system according to claim 12, wherein the transmission-side unit is fixed to the gear housing by being sandwiched between the first gear housing portion and the second gear housing portion on the joint surface.

15. The water detection system according to claim 9, wherein the gear housing includes a recessed portion formed so as to be recessed toward a vertically lower side with the gear housing mounted on the vehicle, and
wherein the transmission-side unit is provided in the recessed portion.

16. The water detection system according to claim 9, wherein the gear housing includes a through-hole formed so as to establish communication between inside and outside the gear housing, and
wherein the transmission-side unit is provided so as to be detachably attachable from outside the gear housing via the through-hole.

17. The water detection system according to claim 9, wherein the ECU housing includes an ECU housing main body portion made from a metallic material, and a resin portion made from a resin material and provided so as to be exposed to outside the ECU housing, and
wherein the reception-side unit is provided in proximity to the resin portion.

18. The water detection system according to claim 17, wherein the resin portion is the connector portion, and
wherein the reception-side unit is provided in proximity to the connector portion.

19. The water detection system according to claim 17, wherein the ECU housing main body portion includes an ECU housing main body opening portion formed so as to expose an inside of the ECU housing,
wherein the ECU housing includes a cover member made from a resin material and closing the ECU housing main body opening portion, and
wherein the reception-side unit is provided in proximity to the cover member.

20. The water detection system according to claim 9, wherein the steering mechanism includes a steering shaft configured to transmit the rotation of the steering wheel, a pinion gear provided at the steering shaft, and a rack bar meshed with the pinion gear and configured to covert a rotation of the pinion gear rotatable according to a rotation of the steering shaft into an axial movement,
wherein the electric power steering apparatus includes a torque sensor provided at the steering shaft and configured to detect a steering torque generated at the steering mechanism,
wherein the torque sensor includes a torsion bar provided at the steering shaft, a detection unit configured to detect a torsional amount of the torsion bar, and a sensor housing containing the detection unit therein, and
wherein the transmission-side unit is provided in the sensor housing.

21. The water detection system according to claim 9, wherein the electric power steering apparatus includes a steering shaft configured to transmit the rotation of the steering wheel, a pinion gear provided at the steering shaft, a rack bar meshed with the pinion gear and configured to covert a rotation of the pinion gear rotatable according to a rotation of the steering shaft into an axial movement, and a ball screw mechanism provided between the rack bar and the electric motor and serving as a speed reducer configured to transmit a rotational force of the electric motor to the rack bar,
wherein the ball screw mechanism includes a wheel turning shaft-side ball screw groove provided on an outer peripheral side of the rack bar and having a helically grooved shape, a nut provided annularly so as to surround the rack bar and configured in such a manner that the rotational force of the electric motor is transmitted thereto, a nut-side ball screw groove provided on an inner peripheral side of the nut, having a helically grooved shape, and forming a ball circulation groove together with the wheel turning shaft-side ball screw groove, and a plurality of balls loaded in the ball circulation groove, and wherein the plurality of balls is displaced in the ball circulation groove according to a rotation of the nut relative to the rack bar, thereby causing the rack bar to be displaced in a longitudinal direction of the rack bar relative to the nut.

22. The water detection system according to claim 21, wherein the gear housing includes a ball screw mechanism containing portion containing the ball screw mechanism therein, and a rack bar containing portion formed so as to cylindrically extend from the ball screw mechanism containing portion to each of a right-side turning target wheel side and a left-side turning target wheel side and containing the rack bar therein, wherein the electric power steering apparatus includes a pair of boots provided at a pair of ends of the rack bar containing portion, respectively, made from a resin material, and configured to prevent or reduce the leak of the water from outside into the gear housing, and wherein the transmission-side unit is positioned closer to any one of the pair of ends than the ball screw mechanism containing portion is.

23. The water detection system according to claim 21, wherein the speed reducer includes an output pulley provided at an output shaft of the electric motor, an input pulley provided at the nut, and a belt or a chain serving as a transmission member provided so as to extend between the output pulley and the input pulley, and wherein the transmission-side unit is provided in a region surrounded by the output pulley, the input pulley, and the transmission member on a plane perpendicular to a rotational axis of the nut.

24. The water detection system according to claim 21, wherein the speed reducer includes an output pulley provided at an output shaft of the electric motor, an input pulley provided at the nut, and a belt or a chain serving as a transmission member provided so as to extend between the output pulley and the input pulley, and wherein the transmission-side unit is provided outside the transmission member on a plane perpendicular to a rotational axis of the nut.

25. The water detection system according to claim 9, wherein the gear housing includes a groove portion formed so as to be recessed toward a vertically lower side and formed so as to extend toward the transmission-side unit side, with the gear housing mounted on the vehicle.

26. The water detection system according to claim 9, wherein the gear housing includes a water holding portion provided in proximity to the transmission-side unit and configured to hold the water.

27. The water detection system according to claim 9, wherein the transmission-side unit includes a regulation portion formed so as to protrude beyond the water detection element toward a facing surface side of the gear housing that faces the water detection element, and configured to regulate a displacement of the water detection element toward the facing surface side of the gear housing.

28. The water detection system according to claim 9, wherein the steering mechanism includes a steering shaft configured to transmit the rotation of the steering wheel, a pinion gear provided at the steering shaft, and a rack bar meshed with the pinion gear and configured to covert a rotation of the pinion gear rotatable according to a rotation of the steering shaft into an axial movement, wherein the gear housing includes a rack bar containing portion formed so as to cylindrically extend toward each of a right-side turning target wheel side and a left-side turning target wheel side and containing the rack bar therein, wherein the electric power steering apparatus includes a pair of boots provided at a pair of ends of the rack bar containing portion, respectively, made from a resin material, and configured to prevent or reduce the leak of the water from outside into the gear housing, and a conductivity addition substance provided in the gear housing, positioned between the pair of opening portions and the transmission-side unit, and configured to increase conductivity of the water by being melted in the water.

29. An electric power steering apparatus comprising:
a ball screw mechanism including:
 a wheel turning shaft configured to turn a turning target wheel according to a rotation of a steering wheel,
 a wheel turning shaft-side ball screw groove provided on an outer peripheral side of the wheel turning shaft and having a helically grooved shape,
 a nut provided annularly so as to surround the wheel turning shaft,
 a nut-side ball screw groove provided on an inner peripheral side of the nut, having a helically grooved shape, and forming a ball circulation groove together with the wheel turning shaft-side ball screw groove, and
 a plurality of balls loaded in the ball circulation groove,
the ball screw mechanism being configured in such a manner that the plurality of balls is displaced in the ball circulation groove according to a rotation of the nut relative to the wheel turning shaft, thereby causing the wheel turning shaft to be displaced in a longitudinal direction of the wheel turning shaft relative to the nut;
an output pulley formed cylindrically so as to surround the wheel turning shaft and configured to rotate according to the rotation of the nut;
an input pulley disposed in such a manner that a second reference axis line corresponding to a rotational axis is radially offset from a first reference axis line, and cylindrically formed, the first reference axis line being a rotational axis of the nut;
a belt provided so as to extend between the output pulley and the input pulley and configured to transmit a rotation of the input pulley to the output pulley;
an electric motor configured to rotationally drive the input pulley;
a gear housing made from a metallic material and containing at least a part of the ball screw mechanism and the wheel turning shaft;
a controller spaced apart from the electric motor and configured to control driving of the electric motor;
a transmission-side unit provided in the gear housing, and including a water detection element configured to detect the water, a transmitter configured to wirelessly transmit an output signal of the water detection element, and a power source configured to supply power to the water detection element and the transmitter; and
a reception-side unit provided in the controller, and including a receiver configured to receive the output signal wirelessly transmitted from the transmitter, and a determination circuit configured to determine, based on the output signal received by the receiver, whether there is a leak of the water into the gear housing.

\* \* \* \* \*